United States Patent
Swain et al.

[11] Patent Number: 6,010,515
[45] Date of Patent: Jan. 4, 2000

[54] DEVICE FOR USE IN TYING KNOTS

[75] Inventors: Paul Swain; Feng Gong; Geoffrey John Brown; Timothy Noel Mills, all of London, United Kingdom

[73] Assignee: University College London, United Kingdom

[21] Appl. No.: 08/806,435

[22] Filed: Feb. 26, 1997

Related U.S. Application Data

[63] Continuation-in-part of application No. 08/397,152, filed as application No. PCT/GB93/01859, Sep. 3, 1993.

[51] Int. Cl.[7] .................................................... A61B 17/04
[52] U.S. Cl. ........................................... 606/148; 600/104
[58] Field of Search ..................................... 606/110, 113, 606/139, 144, 148; 600/101, 104, 153

[56] References Cited

U.S. PATENT DOCUMENTS

| | | |
|---|---|---|
| 1,625,602 | 4/1927 | Gould et al. . |
| 4,198,960 | 4/1980 | Utsugi .......................... 128/6 |
| 4,602,635 | 7/1986 | Mulhollan et al. . |
| 4,616,631 | 10/1986 | Takahashi ..................... 128/6 |
| 4,961,741 | 10/1990 | Hayhurst . |
| 5,025,778 | 6/1991 | Silverstein et al. .......... 128/4 |
| 5,084,058 | 1/1992 | Li . |
| 5,087,263 | 2/1992 | Li . |
| 5,100,415 | 3/1992 | Hayhurst . |
| 5,133,723 | 7/1992 | Li et al. . |
| 5,163,946 | 11/1992 | Li . |
| 5,176,691 | 1/1993 | Pierce . |
| 5,192,287 | 3/1993 | Fournier et al. . |
| 5,217,471 | 6/1993 | Burkhart . |
| 5,259,366 | 11/1993 | Reydel et al. ............... 128/4 |
| 5,269,791 | 12/1993 | Mayzels et al. . |
| 5,324,298 | 6/1994 | Phillips et al. . |
| 5,334,200 | 8/1994 | Johnson . |
| 5,336,227 | 8/1994 | Nakao et al. ............... 606/114 |
| 5,397,326 | 3/1995 | Mangum . |
| 5,403,330 | 4/1995 | Tuason . |
| 5,417,691 | 5/1995 | Hayhurst . |
| 5,423,830 | 6/1995 | Schneebaum et al. ....... 606/115 |
| 5,423,837 | 6/1995 | Mericle et al. . |
| 5,423,847 | 6/1995 | Strong et al. . |
| 5,439,470 | 8/1995 | Li . |
| 5,562,684 | 10/1996 | Kammerer . |
| 5,562,687 | 10/1996 | Chan . |
| 5,571,117 | 11/1996 | Ahn . |
| 5,593,421 | 1/1997 | Bauer . |
| 5,601,576 | 2/1997 | Garrison . |
| 5,601,578 | 2/1997 | Murphy . |
| 5,630,782 | 5/1997 | Adair ........................... 600/133 |
| 5,643,293 | 7/1997 | Kogasaka et al. ........... 606/148 |
| 5,752,964 | 5/1998 | Mericle . |

FOREIGN PATENT DOCUMENTS

| | | |
|---|---|---|
| 0706779 | 4/1996 | European Pat. Off. . |
| 2900265 | 7/1980 | Germany . |
| 2247841 | 3/1992 | United Kingdom . |

*Primary Examiner*—Michael Buiz
*Assistant Examiner*—Tina T. D. Pham

[57] ABSTRACT

A thread guide device is provided which is adapted to be removably or fixedly mounted on the distal end of an endoscope, or which is an integral part thereof. Alternatively, the device may comprise a head joined to the distal end of an elongate shaft that is slidable within the endoscope. The device has a pair of thread guides, for example in the form of longitudinally extending passages, which are laterally spaced from one another. The device permits a knot formed by threads which have passed through the thread guides to be viewed by the endoscope.

6 Claims, 4 Drawing Sheets

DEVICE FOR USE IN TYING KNOTS

RELATED APPLICATION

This application is a continuation-in-part of application Ser. No. 08/397,152, filed Apr. 4, 1995, which is a national stage application under 35 U.S.C. §371 of PCT/GB93/01859 filed Sep. 3, 1993, which has priority of United Kingdom patent application No. 9218752.5 filed Sep. 4, 1992.

FIELD OF THE INVENTION

This invention relates to a device for use in tying knots during surgery carried out using an endoscope, notably a flexible endoscope.

BACKGROUND OF THE INVENTION

It has hitherto proved difficult to tie knots during flexible endoscopy. In effect, the surgeon is operating down a single longitudinally extending channel, and in endeavoring to tie a knot the surgeon encounters the problem that an effective knot generally requires the application of a force along a direction transverse to the channel of the endoscope. The present invention aims to provide a solution to that problem.

SUMMARY OF THE INVENTION

According to the present invention, there is provided an endoscope having a distal end and a proximal end, and a thread guide device. In one embodiment, the thread guide device is in the form of an annular member which surrounds the distal end without impairing the field of view of the endoscope. The thread guide device has a pair of thread guide means which are laterally spaced from one another, thereby permitting a knot formed by threads which have passed through the thread guide means to be viewed by the endoscope.

In a second embodiment, the thread guide device is constructed to be moveable longitudinally with respect to the end of the endoscope. This embodiment may comprise of a head connected to the distal end of an elongate flexible shaft that is axially slidable within an operation channel of the endoscope. The shaft can be manipulated to move the head toward or away from the distal end of the endoscope. The shaft of the thread guide device is inserted through the operation channel of the endoscope such that the head is disposed at the distal end of the endoscope.

DESCRIPTION OF THE ILLUSTRATIVE EMBODIMENTS

Figure 1:
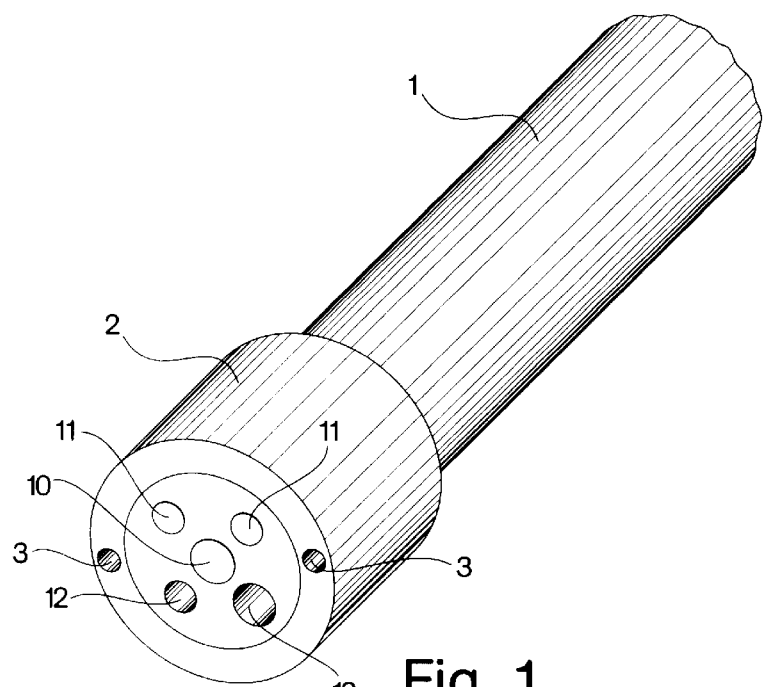
FIG. 1 is a perspective view of a thread guide device according to the first embodiment of the invention mounted on the distal end of an endoscope.

FIG. 1 shows an endoscope 1 having a thread guide device 2 mounted on the distal end thereof. The endoscope itself can be conventional, and the type illustrated has an image bundle 10, two illumination bundles 11, and two operating channels 12. It must be emphasized, however, that other forms of endoscope could be used instead.

The head guide device 2 takes the form of a short tube of circular cross-section, which surrounds the distal end portion of the endoscope 1. The device 2 may be mounted on the endoscope 1 either as a push fit, by providing the device 2 with an internal thread to engage the external thread provided on some conventional endoscopes, or in any other appropriate fashion.

The device 2 has a pair of thread guide passages 3 which extend parallel to the longitudinal axis of the endoscope 1 and device 2 from one end of the device to the other. The passages are sufficiently large in cross-section to permit a thread of the type normally used in surgery to pass therethrough. As illustrated, the two passages 3a are preferably arranged substantially at 180° with respect to one another about the axis of the device 2, but though this is desirable from the point of view of enabling the maximum force to be exerted on the knot which is being tied, it is not essential.

Figure 2:
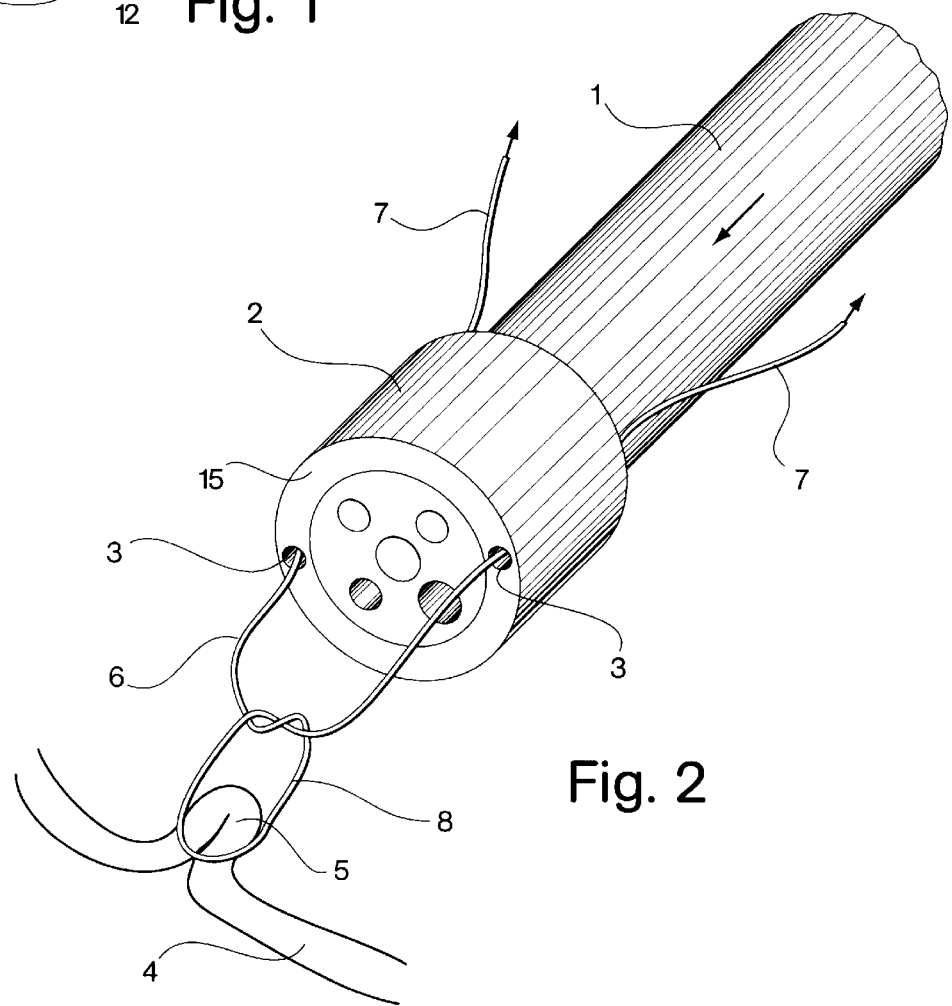
FIG. 2 shows the device and endoscope of FIG. 1, being used to tie a half hitch knot.
Figure 3:
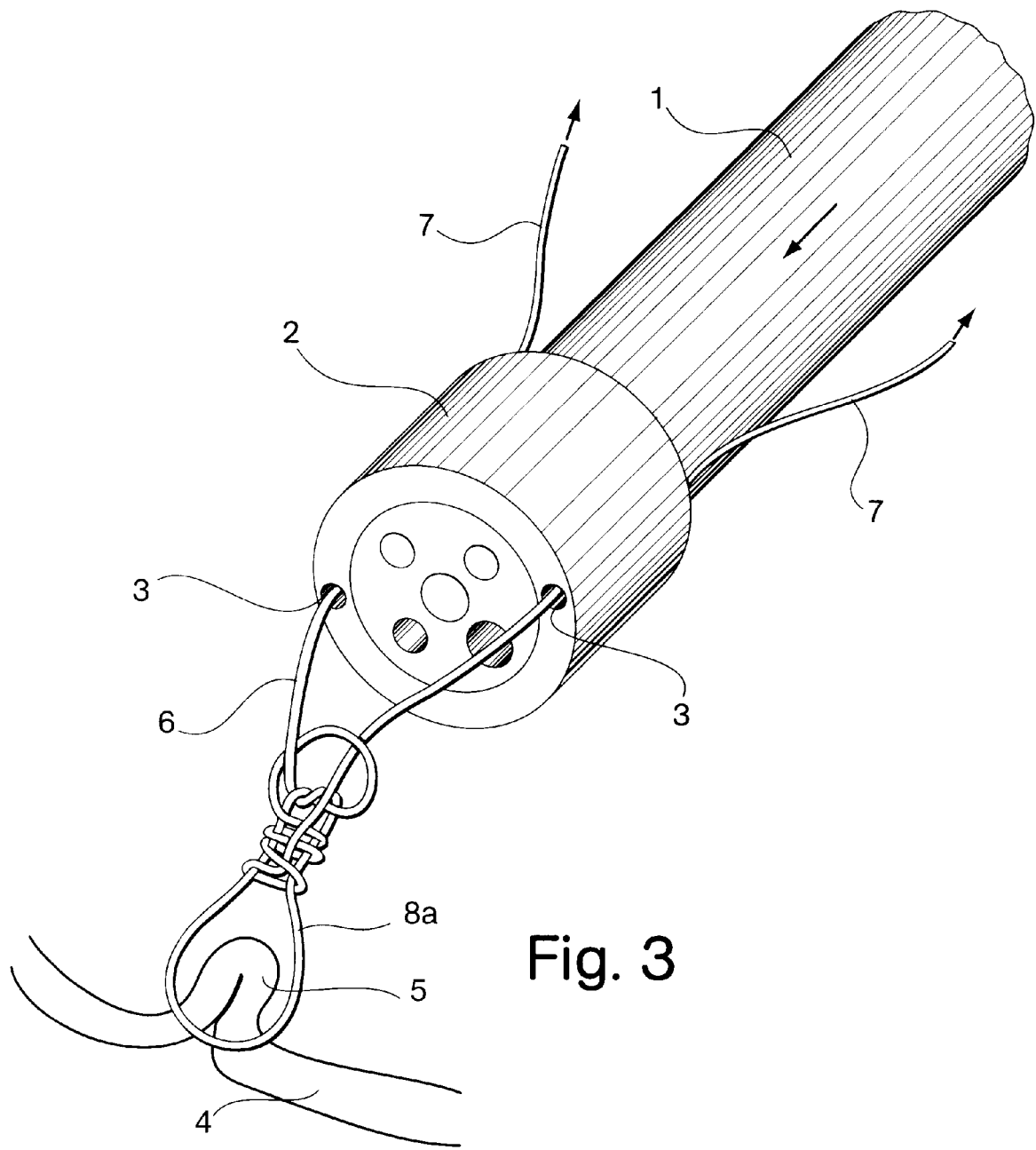
FIG. 3 shows the device and endoscope of FIG. 1 being used to tie a selflock slipknot.

The way in which the arrangement shown in FIG. 1 is used in practice can be seen from FIGS. 2 and 3.

FIG. 2 additionally shows part of a patient's tissue 4, including a U-shaped tissue portion 5 through which a thread 6 has been passed by the surgeon. It is desired to tie a knot 8 in the thread 6. At the start of the knot-typing procedure, the ends 7 of the thread 6 are outside the patient, generally emerging through the mouth or anus. Either before or after the thread guide device 2 is mounted on the endoscope 1, a loose knot is tied outside the patient, using the ends 7, and each of the ends 7 is then passes through a respective one of the passages 3 in a direction from the distal end of the endoscope to the proximal end thereof.

The endoscope with the thread guide device thereon is then introduced into the patient and moved towards the portion of tissues. As this is done the loose knot 8 slides along the thread ends until the distal end of the endoscope is adjacent the portion of tissue 5. The surgeon then pulls on the ends 7 in the direction of the arrows indicated thereon. This causes a force to be exerted on the loose knot 8 which has a lateral component and which therefore tends to tighten the knot. During this whole process the knot can be viewed through the viewing channel of the endoscope, since the knot is directly in front of the viewing channel of the endoscope, and the field of view is not in any way impaired by the thread guide device 2.

The process just described serves to tie a single half hitch knot. It is common practice for a surgical knot to consist of more than one half-hitch, say two or three, and this can be achieved using the arrangement shown in FIG. 2, with the endoscope 1 and thread guide device 2 being withdrawn from the patient and reinserted each time an additional half hitch is made.

FIG. 3 shows the use of the same arrangement as FIG. 2, but to tie a self-lock slipknot 8a. Apart from the differences in the knots themselves, the procedure used is the same as that just described with reference to FIG. 2.

The thread guide device shown in FIGS. 1 to 3 is a component which is distinct from the endoscope itself, and is removable therefrom. However, it would alternatively be possible for the device to be integral with, or permanently secured to, the endoscope.

Figure 4:
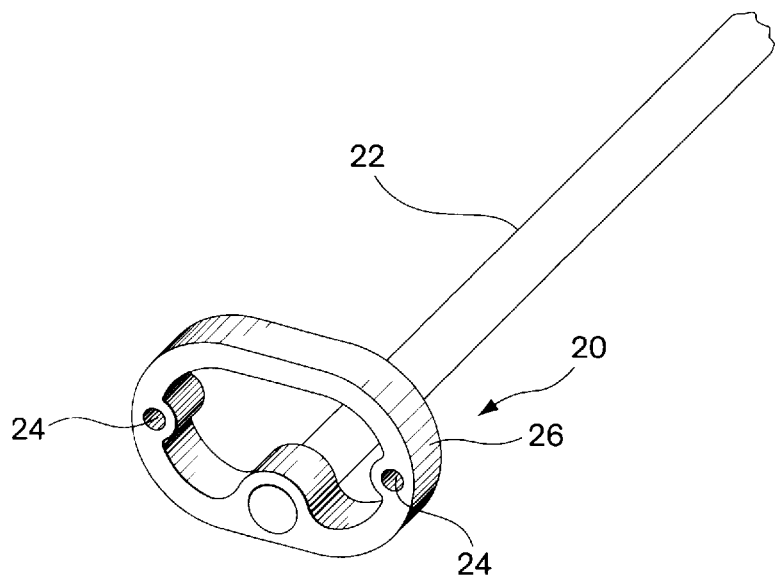
FIG. 4 shows a second embodiment of the thread guide device.

FIG. 4 shows another embodiment of the thread guide device 20. The thread guide device 20 is comprised of a head 26, preferably having an oval shape, that is attached to an elongate flexible shaft 22. The head is preferably fabricated from a rigid material such as ABS plastic. The flexible elongate shaft 22 preferably comprises a stainless steel spring sheath that is fully encapsulated with a plastic material such as PTFE. The head is joined to one end of the shaft by overmolding. The head 26 has a pair of thread guides 24, preferably spaced approximately 180° apart. The thread guides are passages extending through the head, parallel to the longitudinal axis of the shaft and dimensioned to slidably receive suture thread.

Figure 5:
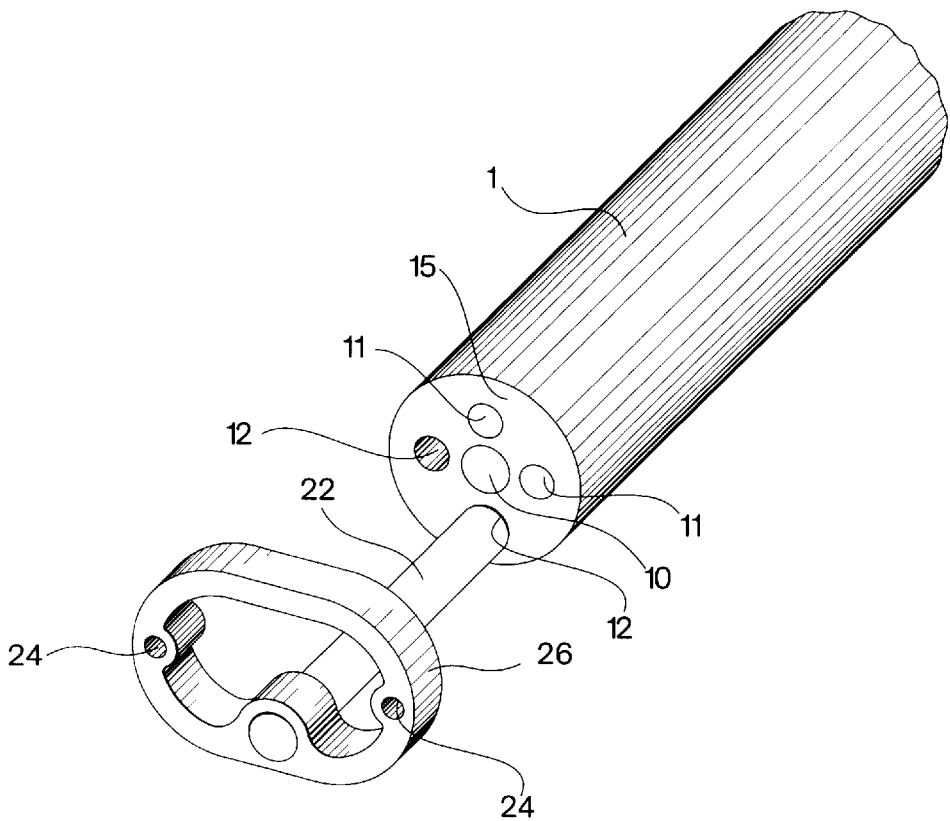
FIG. 5 shows the second embodiment of the thread guide device positioned in an endoscope.

As is shown in FIG. 5, the thread guide device is used in a cooperating arrangement with an endoscope 1. The shaft 22 is inserted into an operation channel 12 from the distal end of an endoscope 1 prior to advancing a knot to a surgical site within a patient. The length of the shaft 22 is at least slightly greater than the length of the endoscope so that its proximal end may be manipulated to control movement of the thread guide device relative to the endoscope. The shaft of the thread guide device 20 is rotatable and axially slidable within the operation channel 12. The range of motion of the device 20 allows the head 24 to be drawn back to contact the distal face 15 of the endoscope and permits movement in a distal direction so that the head may be extended forward, ahead of the endoscope.

Figure 6:
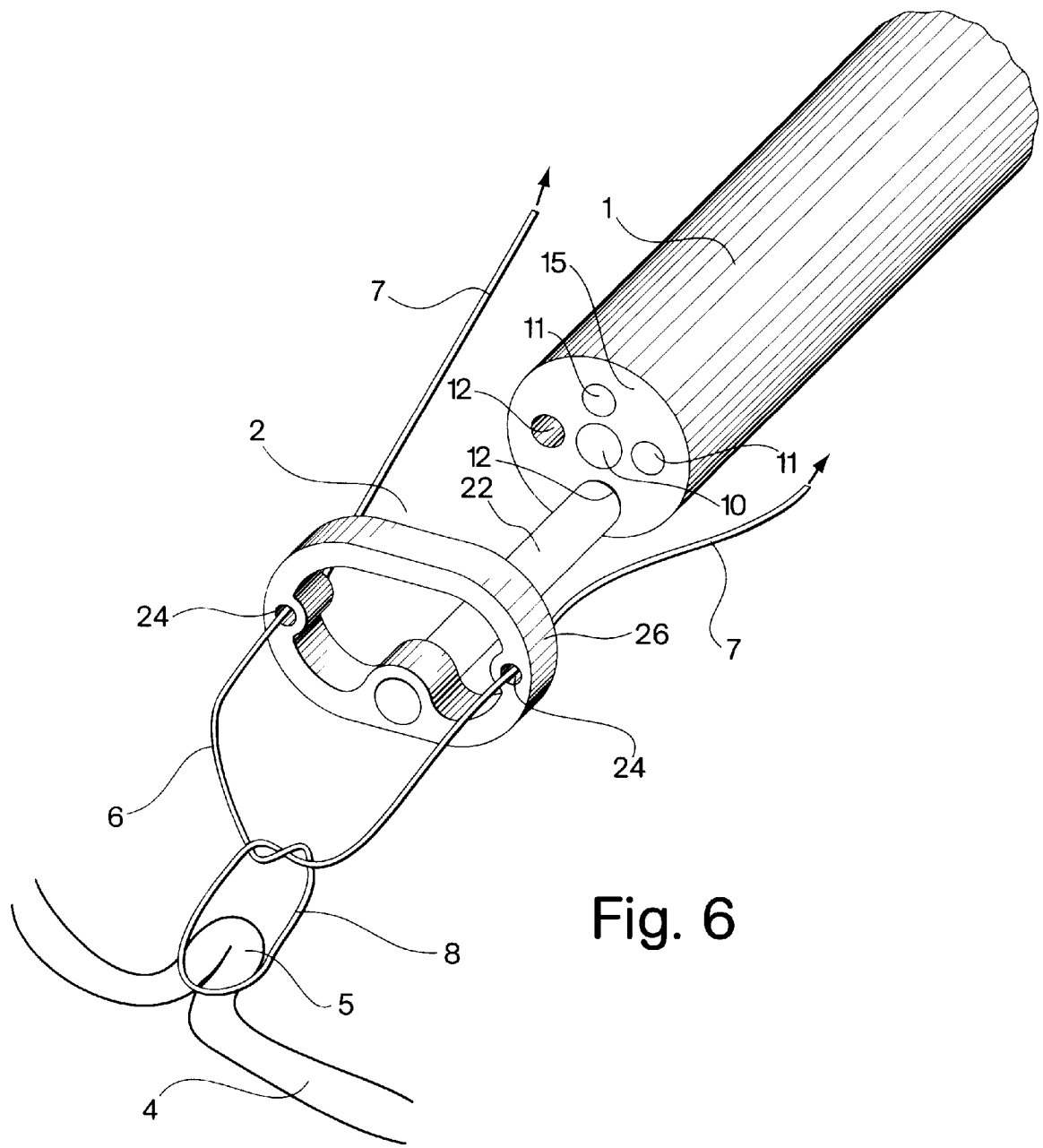
FIG. 6 shows the second embodiment of the device and endoscope being used to tie a half-hitch knot.

FIG. 6 shows the thread guide device in use, inserted into the endoscope with the thread leads 7 passing through the thread guides 24 and with the suture knot 8 positioned in the center and in front of the head 26. The head 26 must be dimensioned to provide an unobstructed view through the ring from the viewing channel 10 of the endoscope 1. Positioning the thread guides approximately 180 degrees apart, along the major axis of the oval shaped head maintains the knot in the center of the oval so that it may be viewed and enables a sufficient lateral force to be exerted on the thread leads 7 to tighten the knot.

It is important that the diameter of the head be large enough to maintain the thread leads 7, passing through thread guides 24, out of the way of the endoscopic viewing channel 10. Additionally, the thread must pass freely through the thread guides, around the distal face 15 and along the sides of the endoscope 1. A head diameter that has been found to provide adequate control of the thread leads 7 places the center line of the thread guides 24 a distance apart that is slightly greater than the diameter of the distal end of the endoscope. However, the distance between the thread guides may be equal to or smaller than the diameter of the distal end of the endoscope without severely limiting the function of the thread guide device.

The operation of the thread guide device to advance a knot to a suture site is similar to the operation described above for the device of the first embodiment. The shaft 22 of the thread guide device is inserted into the operation channel 12 at the distal end of the endoscope 1 prior to insertion into the patient. A knot 8, such as a half-hitch, is formed with the loose ends 7 of the surgical suture string 6 and the ends 7 are inserted through thread guides 24. As the thread leads 7 are held taut, the thread guide device and endoscope combination are inserted into the patient and advanced to the suture site 5. During advancement, the physician may maintain the thread guide device in any axial and rotational position, relative to the endoscope, that is suitable to maintain the desired control and visibility of the knot.

As the device is advanced, the knot 8 is maintained in the center of the head 26 so that it may be viewed from the endoscopic viewing channel 10. Once the suture site has been reached, the knot may be advanced tightly against the tissue by sliding the thread guide device axially in a distal direction, independent of the endoscope. The independent movement of the thread guide device maintains visibility through the viewing channel 10, as the distal face 15 of the endoscope need not be pressed against the tissue to tighten the knot.

The knot 8 remains visible through the endoscope during the entire knot tying process, as the thread guide device does not obstruct viewing through the endoscope. After the knot is advanced to the surgical site, the device may be withdrawn and the process repeated to tie additional knots. Other types of knots, such as a self-lock slipknot may be advanced with this device using the steps described above.

It should be understood that while the foregoing description of the invention is intended to be diagrammatic and illustrative only, other embodiments, modifications and uses may be apparent to those skilled in the art without departing from its spirit.

Having thus described the invention what we desire to claim and secure by Letters Patent is:

1. An endoscope having a distal end and a proximal end, and a thread guide device in the form of an annular member which surrounds the said distal end without impairing the field of view of the endoscope, the thread guide device having a pair of thread guide means which are laterally spaced from one another, the device permitting a knot formed by threads which have passed through the thread guide means to be viewed by the endoscope.

2. An endoscope according to claim 1, wherein the thread guide means are diametrically opposed to one another on opposite sides of the endoscope.

3. An endoscope according to claim 1, wherein the said annular member is cylindrical.

4. An endoscope according to claim 1, wherein each of the thread guide means is in the form of a passage extending through the annular member.

5. An endoscope according to claim 4, wherein the said passages are parallel to one another and to the axis of rotation symmetry of the annular member.

6. A method of pushing a knot to a suture site within a patient comprising:

providing an endoscope;

providing a guide member at the distal end of an endoscope without impairing the field of view of the endoscope, the guide member having a pair of thread guides which are laterally spaced from one another, the device permitting a knot formed by threads which have passed through the thread guide to be viewed through the endoscope;

tying a knot with free ends of a suture outside the patient;

inserting the free ends of the suture through the thread guides;

holding the free ends of the suture while inserting the thread guide device and endoscope into the patient;

pushing the knot to the suture site while permitting unobstructed viewing of the knot through the endoscope.

* * * * *